United States Patent
Meergans et al.

(10) Patent No.: US 9,370,578 B2
(45) Date of Patent: Jun. 21, 2016

(54) DOSAGE FORM COMPRISING LOPINAVIR AND RITONAVIR

(71) Applicant: RATIOPHARM GMBH, Ulm (DE)

(72) Inventors: Dominique Meergans, München (DE); Konstantin Holfinger, München (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/382,499

(22) PCT Filed: Mar. 6, 2013

(86) PCT No.: PCT/EP2013/000659
§ 371 (c)(1),
(2) Date: Sep. 2, 2014

(87) PCT Pub. No.: WO2013/131646
PCT Pub. Date: Sep. 12, 2013

(65) Prior Publication Data
US 2015/0017237 A1    Jan. 15, 2015

(30) Foreign Application Priority Data

Mar. 7, 2012 (EP) .................................. 12001545

(51) Int. Cl.
| | |
|---|---|
| *A61K 47/30* | (2006.01) |
| *B01F 3/12* | (2006.01) |
| *B01F 3/08* | (2006.01) |
| *A61K 47/38* | (2006.01) |
| *A61K 38/55* | (2006.01) |
| *A61K 31/513* | (2006.01) |
| *A61K 9/20* | (2006.01) |
| *A61K 31/427* | (2006.01) |

(52) U.S. Cl.
CPC ............... *A61K 47/38* (2013.01); *A61K 9/2077* (2013.01); *A61K 31/427* (2013.01); *A61K 31/513* (2013.01); *A61K 38/55* (2013.01)

(58) Field of Classification Search
CPC ....................................................... A61K 8/375
See application file for complete search history.

(56) References Cited

U.S. PATENT DOCUMENTS

| | | | |
|---|---|---|---|
| 2001/0051721 A1* | 12/2001 | Dickman | A61K 9/4866 514/269 |
| 2007/0027172 A1* | 2/2007 | Dickman et al. | 514/269 |
| 2007/0059360 A1* | 3/2007 | Jaiswal et al. | 424/464 |
| 2010/0173921 A1* | 7/2010 | Lulla et al. | 514/274 |
| 2011/0306539 A1* | 12/2011 | Shen et al. | 514/1.1 |
| 2013/0142877 A1* | 6/2013 | Nalawade et al. | 424/487 |

FOREIGN PATENT DOCUMENTS

| | | | |
|---|---|---|---|
| WO | WO 2006/129276 | * | 5/2006 |
| WO | WO2010036211 | * | 4/2010 |
| WO | WO 2011/141192 | * | 3/2011 |

OTHER PUBLICATIONS

Katharina et al. Characterization of The Themal Properties of Microcrystalline Cellulose by Modulated Temperature Differential Scanning Calorimetry. Aug. 2001.*
He et al. Mechanistic Study of the Effect of Roller Compaction and Lubricant on Tablet Mechanical Strength. Jul. 2006.*

* cited by examiner

*Primary Examiner* — Adam C Milligan
*Assistant Examiner* — Sarah Alawadi
(74) *Attorney, Agent, or Firm* — Milstein Zhang & Wu LLC

(57) ABSTRACT

The present invention relates to an oral dosage form comprising crystalline lopinavir and crystalline ritonavir. The invention further relates to methods of preparing said oral dosage forms containing the above pharmaceutical active agents.

12 Claims, 1 Drawing Sheet

DOSAGE FORM COMPRISING LOPINAVIR AND RITONAVIR

BACKGROUND OF THE INVENTION

Figure 1:
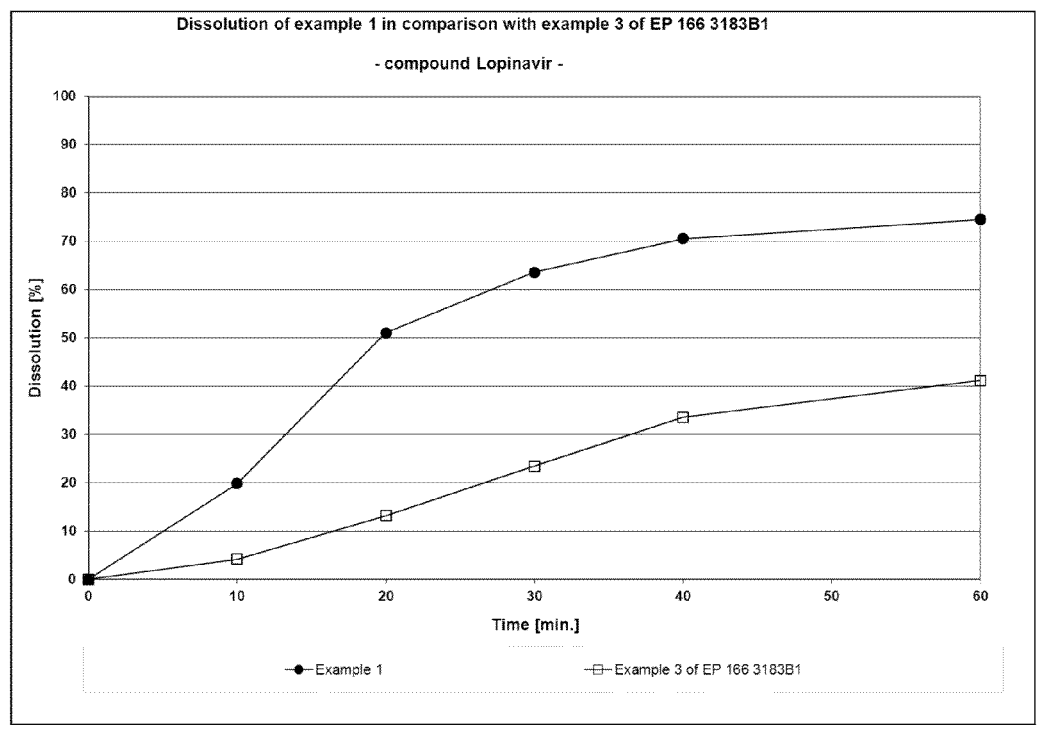

The present invention relates to an oral dosage form comprising crystalline lopinavir and crystalline ritonavir, wherein the crystalline lopinavir is present in a mixture with a brittle vehicle. The invention further relates to methods of preparing said oral dosage forms containing the above pharmaceutical active agents.

"Lopinavir" is reported to be the INN name of (2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide and is characterized by the following chemical formula (I):

formula (I)

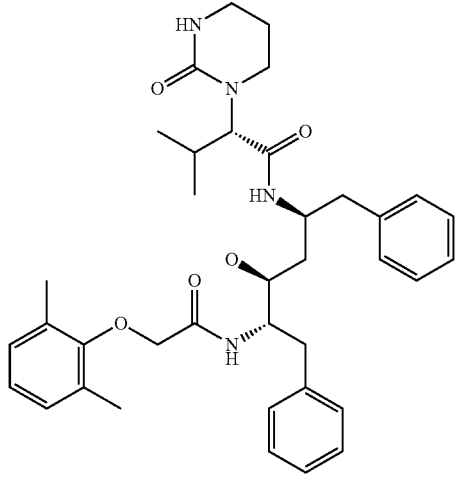

Lopinavir is reported to be an antiretroviral active substance, a member of the protease inhibitors (PI), which are used to treat or prevent infections caused by viruses. Proteases are enzymes used by viruses to cleave proteins for the final assembly of new virions. In the case of lopinavir, especially the prevention of viral replication by inhibiting the activity of proteases, such as HIV-1 protease, are reported.

"Ritonavir" is reported to be the INN name of 1,3-thiazol-5-ylmethylN-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate and is characterized by the following chemical formula (II):

formula (II)

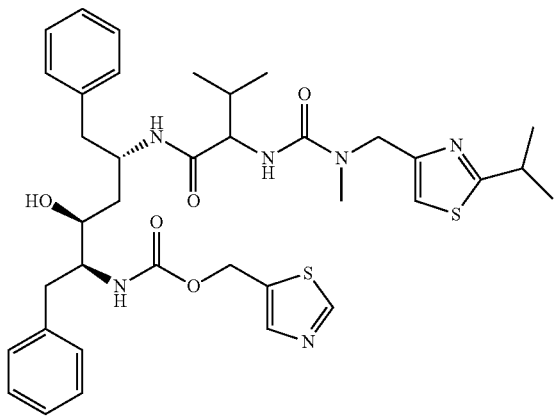

Ritonavir is also reported to be a member of the class of protease inhibitors and is used in the treatment of HIV infection and AIDS. However, ritonavir is frequently described as being used in a combination with other antiretroviral drugs due to its capability to inhibit the same host enzyme that metabolizes other protease inhibitors. Due to this inhibition of the above host enzyme, the plasma concentrations of the further protease-inhibiting drugs tend to be higher so that their dose and frequency in administration can be lowered.

EP 1 663 183 B1 describes a solid pharmaceutical composition comprising ritonavir. The pharmaceutical composition can optionally comprise further protease inhibitors, such as lopinavir, indinavir and saquinavir. However, it turned out that the compositions described in the art show a dissolution and plasma profile which can be improved, especially during the first 30 minutes after administration. Also content uniformity of those compositions is still improvable.

Further, it turned out that the known compositions have to be processed within a very small and specific range of process parameters, i.e. the manufacturing process and thus the quality of the resulting products is device dependent.

Additionally, the storage stability of the prior art compositions is often not satisfactory, especially when stored under conditions of climate zones III and IV. These climate zones are characterized by a temperature of 30° C. and a relative humidity of 35% (climate zone III) and of 70% (climate zone IV).

Hence, it was an object of the present invention to overcome the drawbacks of the prior art compositions. Consequently, an oral dosage form comprising a combination of lopinavir and ritonavir and having superior in-vitro and in-vivo properties should be provided, preferably in combination with excellent content uniformity. Any food effect should be minimized. In particular, an oral dosage form should be provided with improved in-vitro properties, such as excellent dissolution within the first 45 minutes. Further, in the dissolution profile, any lag time should be prevented. The lag time should preferably be prevented even in case the oral dosage form is coated with a commercially obtainable HPMC-coating. The dosage form should comprise only minor amounts of decomposition products. Those advantages should be achievable even under the harsh storage conditions of climate zones III and IV. Further, the dosage form should be producible by a predominantly device-independent manufacturing process.

SUMMARY OF THE INVENTION

According to the present invention, the above objects are solved by an oral dosage form comprising crystalline lopinavir in a mixture with a brittle vehicle and crystalline ritonavir and by a process for producing said dosage form.

Thus, a subject of the present invention is an oral dosage form comprising (a) crystalline lopinavir in a mixture with a brittle vehicle (c), and (b) crystalline ritonavir.

It was found that the oral dosage form of the present invention leads to superior in-vitro and in-vivo properties, for example a superior dissolution profile (in particular within the first 45 minutes) and to superior plasma levels. Further, an improved content uniformity of the drug can be achieved, which can ensure that the appropriate dose can be applied to the patient. The advantages were achievable even after a long storage period under harsh conditions without significant amounts of decomposition.

Another subject of the invention relates to a method for preparing the oral dosage form of the present invention comprising
(i) providing crystalline lopinavir, brittle vehicle and optionally pharmaceutical excipient(s),
(ii) processing the mixture of step (i) wherein it is assured that lopinavir is maintained in a crystalline form,
(iii) optionally granulating the pharmaceutical composition from step (ii),
(iv) mixing the mixture of step (ii) or the granules of step (iii) with crystalline ritonavir and optionally vehicle(s) and/or pharmaceutical excipients,
(v) processing the mixture of step (iv) into an oral dosage form.

DETAILED DESCRIPTION OF THE INVENTION

In the context of this invention, the term "lopinavir" usually refers to (2S)—N-[(2S,4S,5S)-5-[2-(2,6-dimethylphenoxy)acetamido]-4-hydroxy-1,6-diphenylhexan-2-yl]-3-methyl-2-(2-oxo-1,3-diazinan-1-yl)butanamide in accordance with formula (I). In addition, the term "lopinavir" as used in the present application can refer to free lopinavir as well as to its pharmaceutically acceptable salts, hydrates, solvates, polymorphs and mixtures thereof.

In a preferred embodiment of the present invention lopinavir is used in the form of the free lopinavir, i.e. as shown in formula (I).

The term "crystalline" can be used in the context of this invention to designate the state of solid substances in which the components (atoms, ions or molecules, i.e. in the case of crystalline lopinavir the lopinavir molecules) are arranged in an orderly repeating pattern, extending in all three spatial dimensions and thus exhibit a periodic arrangement over a great range (=long-range order).

In contrast to solid non-crystalline substances, e.g. amorphous substances, crystalline substances can be anisotropic. Normally, they have a defined melting point. They can be distinguished from non-crystalline substances experimentally by means of X-ray diffraction, wherein the crystalline substances normally reveal clearly defined interferences, whereas the non-crystalline substances show in most cases only a few diffuse interferences with small diffraction angles.

The crystalline lopinavir (a) in the oral dosage form of the invention may consist of pure crystalline lopinavir (a). Alternatively, it may also contain small amounts of non-crystalline lopinavir components, provided that a defined melting point of crystalline lopinavir can be detected in a DSC. A mixture is preferred, containing 60 to 99.999% by weight of crystalline lopinavir (a) and 0.001 to 40% by weight of non-crystalline lopinavir, more preferably the mixture contains 90 to 99.99% by weight of crystalline lopinavir (a) and 0.01 to 10% of non-crystalline lopinavir, particularly preferably the mixture contains 95 to 99.9% by weight of crystalline lopinavir (a) and 0.1 to 5% of non-crystalline lopinavir.

In a preferred embodiment of the present invention the crystalline lopinavir (a) in the oral dosage form can preferably comprise hydrated polymorphic Form I of lopinavir. In the present application, hydrated Form I of lopinavir is characterized by the following X-ray powder diffraction (XRPD):
  $8.5°\pm0.1°$, $11.1°\pm0.1°$, $14.8°\pm0.1°$, $19.1°\pm0.1°$, $21.2°\pm0.1°$,
  Further characteristic peaks can be found:
  $11.7°\pm0.1°$, $15.3°\pm0.1°$, $21.8°\pm0.1°$, $22.5°\pm0.1°$
Further, it was found that the polymorphic Form I of lopinavir can convert to another polymorphic form of lopinavir, e.g. under storage conditions, namely to polymorphic Form III of lopinavir. Thus, in another preferred embodiment of the present invention the crystalline lopinavir (a) in the oral dosage form can preferably comprise polymorphic Form III of lopinavir. In the present application, Form III is characterized by the following X-ray powder diffraction (XRPD):
  $4.9°\pm0.1°$, $7.3°\pm0.1°$, $12.2°\pm0.1°$, $16.5°\pm0.1°$, $17.7°\pm0.1°$,
  Further characteristic peaks can be found:
  $6.4°\pm0.1°$, $8.8°\pm0.1°$, $12.8°\pm0.1°$, $14.8°\pm0.1°$ In the context of this invention, the term "ritonavir" usually refers to (1,3-thiazol-5-ylmethylN-[(2S,3S,5S)-3-hydroxy-5-[(2S)-3-methyl-2-{[methyl({[2-(propan-2-yl)-1,3-thiazol-4-yl]methyl})carbamoyl]amino}butanamido]-1,6-diphenylhexan-2-yl]carbamate in accordance with formula (II) above. In addition, the term "ritonavir" as used in the present application can refer to ritonavir in the form of the free base as well as to its pharmaceutically acceptable hydrates, salts, solvates, polymorphs and mixtures thereof.

In a preferred embodiment of the present invention the crystalline ritonavir (b) in the oral dosage form can preferably be polymorphic Form I of ritonavir. Form I is disclosed in EP 1 097 148 B1. In the present application, Form I is characterized by the following two-theta angle positions of the characteristic peaks in X-ray powder diffraction (XRPD):
  $3.3°\pm0.1°$, $8.3°\pm0.1°$, $18.1°\pm0.1°$, $21.5°\pm0.1°$
  Further characteristic peaks can be found:
  $6.8°\pm0.1°$, $19.5°\pm0.1°$, $23.5°\pm0.1°$, $24.4°\pm0.1°$ The X-ray diffraction diagrams of the powders are obtained in reflexion configuration (Bragg-Brentano-Geometry). Polymethylmethacrylate (PMMA) carriers are used as sample carrier, with a sample chamber of 20.0 mm in diameter and 1 mm depth. Measurements are performed by means of an X-ray source with copper anode at a generator voltage of 40 KV and 40 mA electric current in a measure circuit of 435.0 mm. The detection is carried out with a fast, highly sensitive and position-sensitive detector (Vantec-1 of Fa. Bruker AXS, Karlsruhe).

It has been unexpectedly found that the above-mentioned problems can be advantageously solved when ritonavir Form I is used, especially since Form II was reported to be more stable.

The crystalline ritonavir (b) in the oral dosage form of the invention may consist of purely crystalline ritonavir (b). Alternatively, it may also contain small amounts of non-crystalline ritonavir components, provided that a defined melting point of crystalline ritonavir can be detected in a DSC. A mixture containing 85 to 99.999% by weight crystalline ritonavir (b) and 0.001 to 15% by weight non-crystalline ritonavir is preferred, more preferred is a mixture containing 90 to 99.99% by weight crystalline ritonavir (b) and 0.01 to 10% non-crystalline ritonavir, particularly preferred is a mixture containing 95 to 99.9% by weight crystalline ritonavir (b) and 0.1 to 5% non-crystalline ritonavir.

The term "vehicle (c)" may refer to a single vehicle (c) or a mixture of more than one vehicle (c). The vehicle (c) can be a substance which is capable of stabilizing a crystalline active pharmaceutical ingredient, preferably lopinavir and ritonavir, especially by acting as a support and/or enclosing said active pharmaceutical ingredient.

In the present invention hydrophilic polymers can preferably be used as vehicle (c). The term "hydrophilic polymers" generally refers to polymers which possess hydrophilic groups. Examples of suitable hydrophilic groups can be hydroxy, sulfonate, carboxylate and quaternary ammonium groups.

The vehicle (c) may, for example, comprise the following polymers: polysaccharides, such as hydroxypropyl methyl cellulose (HPMC), carboxymethyl cellulose (CMC, especially sodium and calcium salts), ethyl cellulose, methyl cellulose, hydroxyethyl cellulose, ethyl hydroxyethyl cellulose, hydroxypropyl cellulose (HPC), hydroxypropyl methyl cellulose acetate succinate (HPMCAS), hydroxypropyl methyl cellulose succinate (HPMCS), hydroxypropyl cellulose acetate succinate (HPCAS), hydroxyethyl methyl cellulose succinate (HEMCS), hydroxyethyl cellulose acetate succinate (HECAS), hydroxypropyl methyl cellulose phthalate (HPMCP), hydroxyethyl methyl cellulose acetate succinate (HEMCAS), carboxymethyl cellulose (CMC), polyvinylpyrrolidone, polyvinyl alcohol, polymers of acrylic acid and their salts, vinyl pyrrolidone/vinyl acetate copolymers (such as Kollidon® VA 64, BASF), gelatine polyalkylene glycols, such as polypropylene glycol or preferably polyethylene glycol, gelatine and mixtures thereof.

The vehicle (c) preferably used can be polyvinylpyrrolidone, preferably with a weight-average molecular weight of 10,000 to 60,000 g/mol, especially 12,000 to 40,000 g/mol, vinylpyrrolidone and vinyl acetate copolymer, especially with a weight-average molecular weight of 45,000 to 75,000 g/mol and/or polymers of acrylic acid and their salts, especially with a weight-average molecular weight of 50,000 to 250,000 g/mol. In addition, HPMC can preferably be used, especially with a weight-average molecular weight of 20,000 to 90,000 g/mol and/or preferably a proportion of methyl groups of 10 to 35% and a proportion of hydroxy groups of 1 to 35%. Likewise, HPC can be preferably used, especially with a weight-average molecular weight of 50,000 to 100,000 g/mol. Also, polyethylene glycol with a weight-average molecular weight of 2,000 to 40,000 g/mol, especially from 3,500 to 25,000 g/mol, can preferably be used. Likewise, a polyethylene/polypropylene block copolymer can preferably be used wherein the polyethylene content can preferably be 70 to 90% by weight. The polyethylene/polypropylene block copolymer preferably has a weight-average molecular weight of 1,000 to 30,000 g/mol, more preferably from 3,000 to 15,000 g/mol. More preferably, microcrystalline cellulose as well as silicified microcrystalline cellulose can be used, especially when it possesses a weight-average molecular weight of 100,000 to 750,000 g/mol, in particular 125,000 to 650,000 g/mol. The weight-average molecular weight can usually be determined by means of gel permeation chromatography.

In a preferred embodiment, the vehicle (c) used can be a copolymer of vinylpyrrolidone and vinyl acetate, especially with a weight-average molecular weight of 45,000 to 75,000 g/mol. The copolymer can be characterised by the following structural formula (III):

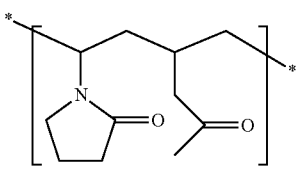

formula (III)

Likewise, it can preferably be possible to use sugar alcohols such as mannitol, sorbitol, xylitol as vehicles (c).

Generally, a pharmaceutical excipient (such as a vehicle) can be a non-brittle or a brittle vehicle excipient. In the present invention it is essential that at least one brittle vehicle is present. In addition, a further non-brittle vehicle can be present.

Pharmaceutical excipients, such as vehicles, can generally be classified with regard to the change in the shape of the particles under compression pressure (compaction): plastic excipients are characterised by plastic deformation, whereas when compressive force is exerted on brittle substances, the particles tend to break into smaller particles. Brittle behaviour on the part of the substrate can be quantified by the increase in the surface area in a moulding. In the art, it is customary to classify the brittleness in terms of the "yield pressure". According to a simple classification, the values for the "yield pressure" here are low for plastic substances but high in the case of friable substances (Duberg, M., Nyström, C., 1982, "Studies on direct compression of tablets VI. Evaluation of methods for the estimation of particle fragmentation during compaction.", Acta Pharm. Suec. 19, 421-436; Humbert-Droz P., Mordier D., Doelker E., "Méthode rapide de determination du comportement à la compression pour des études de prèformulation.", Pharm. Acta Helv., 57, 136-143 (1982)). The "yield pressure" describes the pressure that has to be reached for the excipient (i.e. preferably the vehicle) to begin to flow plastically.

The "yield pressure" is preferably calculated by using the reciprocal of the gradient of the Heckel plot, as described in York, P., Drug Dev. Ind. Pharm. 18, 677 (1992). The measurement in this case is preferably made at 25° C. and at a deformation rate of 0.1 mm/s.

In the context of the present invention, an excipient (especially a vehicle) is deemed a non-brittle excipient when it has a "yield pressure" of not more than 120 MPa, preferably not more than 100 MPa, particularly preferably 5 to 80 MPa. An excipient is usually described as a brittle excipient when it has a "yield pressure" of more than 80 MPa, preferably more than 100 MPa, particularly preferably more than 120 MPa, especially more than 150 MPa. Brittle excipients may exhibit a "yield pressure" of up to 300 MPa or up to 400 MPa or even up to 500 MPa.

Examples of non-brittle excipients (vehicles) are mannitol, povidone, copovidone or starch.

Examples of brittle excipients (vehicles) are calcium hydrogen phosphate, silicates or aluminosilicates, silicified microcrystalline cellulose and microcrystalline cellulose.

The crystalline lopinavir (a) is present in a mixture with a brittle vehicle (c). This mixture can be regarded as an intermediate or as an intragranular phase. The intermediate preferably is further processed to give the final oral dosage form.

In a preferred embodiment, crystalline lopinavir can be distributed substantially homogeneously on and/or in the brittle vehicle (c). It is particularly preferred that lopinavir is adsorbed on the surface of the brittle vehicle (c).

This means that in the mixture of crystalline lopinavir and brittle vehicle, lopinavir can preferably be applied to and/or deposited in the brittle vehicle. The expression "applied to" in this context means bound to the surface of the vehicle by physicochemical interactions, such as van der Waals forces, hydrogen bonds, or charge transfer interactions. It is preferable that at least 50%, more preferably at least 70%, even more preferably at least 90%, especially at least 95% of the brittle vehicle is in contact with lopinavir.

The lopinavir applied to the brittle vehicle (c) and/or deposited in the vehicle can preferably be present in solid form. Lopinavir is preferably present in solid form in the above mixture.

In a further preferred embodiment the brittle vehicle (c) can be an inorganic substance or an organic polymer, preferably an organic polymer.

Organic polymers used as brittle vehicle (c) can be preferably hydrophilic organic polymers. This means polymers which possess hydrophilic groups. Examples of suitable hydrophilic groups are hydroxy, alkoxy, acrylate, methacrylate, sulphonate, carboxylate and quaternary ammonium groups. Hydroxy groups are preferred.

In addition, the organic polymer to be used as vehicle (c) preferably has a weight-average molecular weight of 5,000 to 1,00,000 g/mol, more preferably from 10,000 to 150,000 g/mol. The weight-average molecular weight is preferably determined in the context of this application by means of gel permeation chromatography. When the polymer used in the preparation of the intermediate is dissolved in water in an amount of 2% by weight the resulting dispersion preferably has a viscosity of 0.1 to 18 mPa×s, more preferably 0.5 to 15 mPa×s, especially 1 to 8 mPa×s, measured at 25° C. and preferably determined in accordance with Ph. Eur. 6.0, Chapter 2.2.10.

Further, in a preferred embodiment, the organic polymer (c) being present in the mixture with crystalline lopinavir can preferably be an organic polymer having a glass transition temperature (Tg) of 50-200° C., preferably 60-150° C., particularly 75-120° C.

In a further preferred embodiment, the organic polymer (c) being present in the mixture with crystalline lopinavir can preferably be an organic polymer having a melt temperature (Tm) of 80-300° C., preferably 100-290° C., particularly 180-280° C.

The term "glass transition temperature" (Tg) is used to describe the temperature at which amorphous or partially crystalline polymers change from the solid state to the liquid state. In the process, a distinct change in physical parameters, for example hardness and elasticity, occurs. Below the glass transition temperature a polymer is usually glassy and hard, whereas above the glass transition temperature it changes into a rubber-like to viscous state. The glass transition temperature is determined in the context of this invention by means of dynamic differential scanning calorimetry (DSC).

For this purpose a Mettler Toledo DSC 1 apparatus can be used. The work is performed at a heating rate of 1-20° C./min, preferably 10° C./min, and at a cooling rate of 5-50° C./min, preferably 50° C./min.

In a further preferred embodiment the organic polymer (c) present in the mixture with crystalline lopinavir can be silicified microcrystalline cellulose or microcrystalline cellulose. Especially preferred is microcrystalline cellulose In a further preferred embodiment, calcium hydrogen phosphate, silicates or aluminosilicates can be used a brittle vehicle (c).

In a preferred embodiment, silica, such as Aerosil® 200, is not regarded as brittle vehicle (c).

It is further preferred that brittle and non-water-soluble substances are used as vehicle (c) being present in the mixture with crystalline lopinavir.

In a preferred embodiment of the invention the vehicle (c) comprises a brittle organic polymer and/or a brittle inorganic substance, preferably a brittle non-water-soluble organic polymer and/or a brittle non-water-soluble inorganic substance, preferably a brittle non-water-soluble organic polymer. A non-water-soluble substance generally is a pharmaceutical excipient as specified in the European Pharmacopoeia, with a water solubility of less than 33 mg/ml, measured at 25° C. Preferably, the non-water-soluble substance has a solubility of 10 mg/ml or less, more preferably 5 mg/ml or less, especially 0.01 to 2 mg/ml (determined according to Column Elution method pursuant to EU Directive RL67-548-EWG, Appendix V Chapt. A6).

In a preferred embodiment the crystalline lopinavir (a) comprised in the oral dosage form of the present invention can have an average particle size (D50) of 0.3 to 50 µm, preferably 0.5 to 40 µm, more preferably 1.0 to 25 µm, particularly preferably 1.5 to 20 µm.

Further, the crystalline lopinavir comprised in the oral dosage form can have a D10-value of the particle size distribution of 0.1 to 15 µm, preferably 0.2 to 10 µm, more preferably 0.25 to 6 µm, particularly preferably 0.3 to 2 µm.

Further, the crystalline lopinavir comprised in the oral dosage form can have a D90-value of the particle size distribution of 2 to 200 µm, preferably 4 to 125 µm, more preferably 8 to 75 µm, particularly preferably 12 to 60 µm.

It turned out that an improved dissolution profile and superior plasma level of lopinavir can be achieved without the need of converting the active agent into an amorphous form. Thus, the crystalline lopinavir being present in the mixture with the brittle vehicle and having preferably the above-mentioned average particle size does not exhibit the non-desired properties generally related to active agents in amorphous form such as poor processability and reduced storage stability.

In another embodiment of the present invention the crystalline ritonavir comprised in the oral dosage form of the present invention can have an average particle size (D50) of 0.5 to 150 µm, preferably 0.7 to 75 µm, more preferably 1.0 to 20 µm, particularly preferably 1.2 to 10 µm.

Further, the crystalline ritonavir comprised in the oral dosage form can have a D10-value of the particle size distribution of 0.1 to 15 µm, preferably 0.2 to 7 µm, more preferably 0.3 to 3 µm, particularly preferably 0.4 to 1 µm.

Further, the crystalline ritonavir comprised in the oral dosage form can have a D90-value of the particle size distribution of 2 to 250 µm, preferably 5 to 100 µm, more preferably 7 to 40 µm, particularly preferably 10 to 25 µm.

The term "average particle size" usually refers to the D50-value of the particle size distribution. The particle distribution can be determined by means of laser diffractometry. In particular, a Malvern Instruments Mastersizer 2000 can be used to determine the size (preferably wet measurement with ultrasound 60 sec., 2,000 rpm, preferably dispersed in water, obscuration 4%, the evaluation being performed according to Mie Model).

The average particle size (D50), which is also denoted D50-value of the integral volume distribution, is defined in the context of this invention as the particle diameter at which 50 percent by volume of the particles have a smaller diameter than the diameter which corresponds to the D50-value. Likewise, 50 percent by volume of the particles have a larger diameter than the D50-value. Analogously, the D90-value of the integral volume distribution is defined as the particle diameter at which 90 percent by volume of the particles have a smaller diameter than the diameter which corresponds to the D90-value. Correspondingly, the D10-value of the integral volume distribution is defined as the particle diameter at which 10 percent by volume of the particles have a smaller diameter than the diameter which corresponds to the D10-value.

In a particularly preferred embodiment the oral dosage form of the present invention comprises the combination of lopinavir and ritonavir as sole pharmaceutical active agents. In an alternative embodiment the pharmaceutical composition of the invention can comprise lopinavir and ritonavir in combination with further pharmaceutical active agent(s). In case that the oral dosage form of the invention comprises lopinavir and ritonavir in combination with further pharmaceutical active agents, the further pharmaceutical active agent(s) is preferably selected from zidovudine, lamivudin, tenofovir and/or abacavir.

Preferably, the oral dosage form of the present invention comprises 20 mg to 500 mg lopinavir, more preferably 30 mg to 400 mg lopinavir, still more preferably 40 mg to 300 mg lopinavir, particularly preferably 50 mg to 250 mg lopinavir. The amounts generally refer to "free" lopinavir (i.e. when lopinavir is present in form of a salt or a solvate, the corresponding amount has to be added accordingly).

Preferably, the oral dosage form of the present invention comprises 5 mg to 150 mg ritonavir, more preferably 10 mg to 125 mg ritonavir, still more preferably 15 mg to 100 mg ritonavir, particularly preferably 20 mg to 75 mg ritonavir. The amounts generally refer to "free" ritonavir (i.e. when ritonavir is present in form of a salt or a solvate, the corresponding amount has to be added accordingly).

In a preferred embodiment the oral dosage form of the invention can comprise crystalline lopinavir (a) and brittle vehicle (c), wherein the weight ratio of crystalline lopinavir (a) to brittle vehicle (c) can be from 1:10 to 10:1, preferably from 1:7 to 7:1, more preferably from 1:5 to 5:1 and particularly from 1:3 to 2:1.

In a preferred embodiment the vehicle (c) can be present in an amount of 5 to 75 wt %, preferably 10 to 70 wt %, more preferably 15 to 65 wt %, based on the total weight of the oral dosage form.

In a preferred embodiment the oral dosage form can further comprise one or more pharmaceutical excipient(s) (d).

Examples of pharmaceutical excipients are glidants, fillers, binders, disintegrants, surfactants and lubricants.

Glidants can be used to improve the flowability. For example, talc can be used as glidant. More preferably, silica (for example Aerosil®) is used. Preferably, the glidant can be present in an amount of up to 3 wt %, in particular, 0.1 to 2 wt %, based on the oral dosage form. Preferably, the silica has a specific surface area of 50 to 400 $m^2/g$, measured by gas adsorption according to Ph. Eur., 6.0, Chapter 2.9.26.

Fillers can be used to increase the bulk volume and weight of a low-dose drug to a limit at which a pharmaceutical dosage form can be formed. Fillers may fulfil several requirements, such as being chemically inert, non-hygroscopic, biocompatible, easily processable and may possess good biopharmaceutical properties. Examples of fillers are lactose, sucrose, glucose, mannitol, calcium carbonate, cellulose and others.

The fillers can be present in the oral dosage form of the present invention in an amount of 0 to 50 wt %, preferably 1 to 35 wt %, more preferably 5 to 30 wt % and still more preferably 10 to 25 wt % of the total weight of the oral dosage form.

Binders usually are regarded as substances for ensuring that the oral dosage form (in particular the tablet) can be formed with the required mechanical strength. In the present invention preferably organic polymers, which are described above as vehicle (c), also act as binders.

Disintegrants usually are compounds, which can enhance the ability of the intermediate to break into smaller fragments when in contact with a liquid, preferably water. Preferred disintegrants are sodium carboxymethyl starch, cross-linked polyvinylpyrrolidone (Crospovidone), sodium carboxymethyl glycolate (for example Explotab®), swelling polysaccharide, for example soy polysaccharide, carrageenan, agar, pectin, starch and derivates thereof, protein, for example formaldehyde-casein, sodium bicarbonate or mixtures thereof. Crospovidone is particularly preferred.

The disintegrant can be present in the oral dosage form of the present invention in an amount of 0 to 20 wt %, preferably 1 to 17 wt %, more preferably 3 to 15 wt % and still more preferably 7 to 12 wt % of the total weight of the oral dosage form.

Surfactants usually are substances which lower the interfacial tension between two phases, thus enabling or supporting the formation of dispersions or working as a solubilizer. Common surfactants can be alkyl sulfates (for example sodium lauryl sulfate), alkyltrimethylammonium salts, alcohol ethoxylates, sorbitanes and the like. Sorbitans are preferred and sorbitan monododecanoate is especially preferred.

The surfactant can be present in the oral dosage form of the present invention in an amount of 0 to 10 wt %, preferably 0.1 to 8 wt %, more preferably 0.3 to 5 wt % and still more preferably 0.7 to 4.0 wt % of the total weight of the oral dosage form.

Lubricants are generally used in order to reduce sliding friction. In particular, the intention is to reduce the sliding friction found during tablet pressing between the punch moving up and down in the die and the die wall on the one hand, and between the edge of the tablet and the die wall on the other hand. Suitable lubricants are, for example, stearic acid, adipic acid, sodium stearyl fumarate and/or magnesium stearate. Sodium stearyl fumarate is particularly preferred.

Lubricants can preferably be used in an amount of up to 3% by weight, preferably 0.1 to 2 wt %, based on the total weight of the dosage form.

It lies in the nature of pharmaceutical excipients that they sometimes can perform more than one function in a pharmaceutical formulation. Therefore, the vehicle (c) may act as excipient (d) and vice versa. For example, povidone may act both as vehicle and binder. However, in order to provide an unambiguous delimitation, the fiction will therefore preferably apply that a substance which is used as a particular excipient is not simultaneously also used as a further pharmaceutical excipient. For example, microcrystalline cellulose—if used as a vehicle (c)—is not also used for example as a disintegrant (even though microcrystalline cellulose also exhibits a certain disintegrating effect).

In a preferred embodiment of the invention the mixture of crystalline lopinavir (a) and brittle vehicle (c) is obtained by a milling process, preferably by a co-milling process.

In a preferred embodiment of the invention, the mixture of the crystalline lopinavir (a) and the brittle vehicle (c) can be regarded as intragranular phase. Further, the phase containing crystalline ritonavir can be preferably regarded as extragranular phase.

In a preferred embodiment the oral dosage form of the invention can preferably comprise an intragranular phase comprising crystalline lopinavir (a), brittle vehicle (c) and one or more excipient(s) (d), and an extragranular phase comprising crystalline ritonavir (b), optionally vehicle (c) and further excipient(s) (d).

In an alternative preferred embodiment the extragranular phase can comprise one or more active agent(s), preferably selected from zidovudine, lamivudine, tenofovir and/or abacavir.

The optional vehicle (c) in the extragranular phase can generally be a non-brittle and/or a brittle vehicle (c). The brittle vehicle (c) in the extragranular phase can preferably be the same and/or another brittle vehicle (c) comprised in the intragranular phase. Preferably, the extragranular phase comprises a non-brittle vehicle (c). In a preferred embodiment ritonavir (b) is adsorbed on the surface of the non-brittle vehicle (c). The adsorption may be achieved by co-blending ritonavir and non-brittle vehicle (c).

In case the intragranular phase comprises crystalline lopinavir (a) and an inorganic substance as vehicle (c), the intragranular phase preferably does not comprise any further excipients. In particular, in this case the intragranular phase preferably does not comprise a water-soluble polymer.

In case the intragranular phase comprises non-crystalline lopinavir (a) and an organic polymer, in particular microcrystalline cellulose as vehicle (c), the intragranular phase preferably comprises one further excipient, such as a glidant.

The extragranular phase can preferably comprise more vehicle(s) (c). In a preferred embodiment, the extragranular phase preferably comprises at least one non-brittle vehicle and at least one brittle vehicle. The at least one non-brittle vehicle (c), comprised in the extragranular phase, can preferably be an organic polymer which preferably can also have binding properties. For example, the non-brittle vehicle (c) in the extragranular phase can preferably be polyvinylpyrrolidone, HPMC or a vinylpyrrolidone vinyl acetate copolymer, e.g. with a weight-average molecular weight of 25,000 to 80,000 g/mol. Vinylpyrrolidone vinylacetate copolymer is particularly preferred.

In a preferred embodiment the oral dosage form of the present invention can preferably comprise the following amounts of components:
5 to 40 wt %, preferably 10 to 35 wt %, more preferably 15 to 25 wt % lopinavir (a),
1 to 10 wt %, preferably 2 to 9 wt %, more preferably 4 to 8 wt % ritonavir (b),
5 to 75 wt %, preferably 10 to 60 wt %, more preferably 15 to 45 wt % vehicle (c),
0 to 1 wt %, preferably 0.01 to 0.8 wt %, more preferably 0.02 to 0.5 wt % glidant,
0 to 40 wt %, preferably 10 to 35 wt %, more preferably 15 to 30 wt % filler,
0 to 20 wt %, preferably 3 to 17 wt %, more preferably 5 to 12 wt % disintegrant,
0 to 20 wt %, preferably 2 to 15 wt %, more preferably 4 to 10 wt % surfactant,
0 to 3 wt %, preferably 0.3 to 2.5 wt %, more preferably 0.5 to 2.0 wt % lubricant,
wherein the wt % are based on the total weight of the dosage form.

In a preferred embodiment, the oral dosage form of the present invention preferably comprises:
an internal phase comprising
5 to 40 wt %, preferably 10 to 35 wt %, more preferably 15 to 25 wt % lopinavir (a), 2 to 55 wt %, preferably 5 to 45 wt %, more preferably 10 to 35 wt % brittle vehicle (c), wherein the brittle vehicle (c) is preferably a brittle organic polymer, more preferably microcrystalline cellulose, and further preferably does not comprise a water-soluble polymer;
0 to 1 wt % of a glidant, preferably fumed silica,
and an external phase comprising
1 to 10 wt %, preferably 2 to 9 wt %, more preferably 4 to 8 wt % ritonavir (b), 0 to 50 wt %, preferably 2 to 45 wt %, more preferably 5 to 40 wt % vehicle (c), wherein the vehicle (c) preferably comprises a non-brittle substance, more preferably an hydrophilic polymer, in particularly povidone or copovidone or HPMC, and, optionally, a brittle substance, preferably an aluminosilicate and/or microcrystalline cellulose, wherein the ratio of non-brittle substance to brittle substance is preferably between 4:10 to 1:25,
0 to 40 wt %, preferably 10 to 35 wt %, more preferably 15 to 30 wt % filler,
0 to 20 wt %, preferably 3 to 17 wt %, more preferably 5 to 12 wt % disintegrant,
0 to 20 wt %, preferably 2 to 15 wt %, more preferably 4 to 10 wt % surfactant, in particular, sorbitane monododecanoate,
0 to 3 wt %, preferably 0.3 to 2.5 wt %, more preferably 0.5 to 2.0 wt % lubricant,
wherein the wt % are based on the total weight of the dosage form.

In a preferred embodiment the oral dosage form of the present invention is in the form of a capsule or a tablet. In case of the form of a capsule, the present dosage form is preferably in the form of a hard-shell or soft-shell capsule. Alternatively, the dosage form can be present in form of a powder or preferably granulate, which is stored in a sachet or stick-pack.

In particular, the oral dosage form of the present invention is a tablet, preferably a tablet for peroral use. Alternatively, it could be a dispersing tablet or an oral dispersible tablet (ODT).

Another subject of the present invention is a method for preparing an oral dosage form according to the present invention comprising the steps of
(i) providing crystalline lopinavir, brittle vehicle (c) and/or pharmaceutical excipient (d),
(ii) processing the mixture of step (i) wherein it is assured that the lopinavir is maintained in the crystalline form,
(iii) optionally granulating the lopinavir of step (i) or the mixture of step (ii),
(iv) mixing the mixture of step (i) or the processed mixture of step (ii) or the granules of step (iii) with crystalline ritonavir (b) and mixing the mixture of step (ii) or the granules of step (iii) with crystalline ritonavir (b), optionally vehicle(s) (c) and/or pharmaceutical excipient(s) (d),
(v) processing the mixture of step (iv) into an oral dosage form.

In principle, all explanations given above for preferred embodiments of the oral dosage form of the present invention also apply for the process of the present invention.

Generally, in step (i) crystalline lopinavir can be present in an amount of 20 to 80 wt %, preferably 22 to 75 wt %, more preferably 27 to 70 wt %, and particularly preferred between 30 and 65 wt %, based on the total weight of the mixture resulting from step (i).

Generally, in step (i), the vehicle (c) can be present in an amount of 20 to 80 wt %, preferably 25 to 73 wt %, more preferably 30 to 66 wt %, and particularly preferred between 35 and 60 wt %, based on the total weight of the mixture resulting from step (i)

Generally, in step (i) a further excipient, preferably a glidant, more preferably fumed silica, can be preferably present in an amount of 0 to 20 wt %, preferably 0.5 to 15 wt %, more preferably 1 to 12 wt %, and particularly preferred between 1.5 and 10 wt %, based on the total weight of the mixture resulting from step (i).

Especially preferred vehicles (c) in these embodiments can be brittle organic polymers, preferably microcrystalline cellulose or silicified microcrystalline cellulose.

In step (ii) the mixture of step (i) is processed wherein it is assured that the lopinavir is maintained in a crystalline form. This means that the process conditions of step (ii) have to be chosen such that crystalline lopinavir is not transformed into non-crystalline lopinavir. In a preferred embodiment process step (ii) preferably comprises a milling process, preferably a co-milling process.

The milling conditions are preferably selected such that the lopinavir is maintained in crystalline form.

The milling can be generally performed in conventional milling apparatuses, such as in a ball mill, air jet mill, pin mill, classifier mill, cross beater mill, disk mill, mortar grinder, rotor mill. A planetary ball mill, such as PM 100 from Retsch® is preferably used.

The milling time is usually 0.5 minutes to 10 hours, preferably 30 minutes to 8 hours, more preferably 1 hour to 7 hours, particularly 1.5 to 5 hours.

It was unexpectedly found that milling only one of the active agents, namely lopinavir, instead of both active agents significantly increases the desirable properties of the resulting dosage form, in particular when lopinavir is co-milled together with the brittle vehicle (c).

Mixing of the substances provided in step (i) can preferably be conducted before the milling process. The mixing can be carried out with conventional mixing devices, e.g. in a free fall mixer like Turbula® T 10B (Bachofen AG, Switzerland). Mixing can be carried out, e.g., for 1 minute to 1 hour, preferably for 5 to 30 minutes.

In a further preferred embodiment, in optional step (iii) the mixture resulting from milling step (ii) is granulated.

The mixture resulting from milling step (ii) can preferably be further processed in a granulating step (iii), preferably in a dry granulation step. The dry granulation can preferably be carried out by "slugging", for example by using a rotary press. Preferably, roller compaction is used, for example roller compactors from Powtec or Alexanderwerk. After compaction, the slugs usually are broken up to granules, for example with a hammer mill.

In a preferred embodiment the granulation conditions in step (iii) are chosen such that the resulting granulated pharmaceutical composition can comprise an average particle size (D50) of 10 to 500 µm, more preferably of 30 to 250 µm, furthermore preferably of 50 to 200 µm, most preferably of 70 to 170 µm.

The bulk density of the granulated pharmaceutical composition resulting from step (iii) of the process of the present invention can usually range from 0.2 to 0.85 g/ml, preferably from 0.25 to 0.85 g/ml, more preferably from 0.3 to 0.75 g/ml.

The mixture of step (ii) or the granules of step (iii), comprising crystalline lopinavir, can be regarded as "intragranular phase".

In step (iv), the processed mixture of step (ii) or the granules of step (iii) are mixed with crystalline ritonavir (b) and optionally vehicle (c) and/or further excipient(s) (d).

The mixing (iv) can be carried out with mixing devices, e.g. in a free fall mixer like Turbula® T 10B (Bachofen AG, Switzerland). Mixing can be carried out for example for 1 minute to 1 hour, preferably for 5 to 30 minutes.

The vehicle (c) used in the mixing step (iv) can preferably be a mixture of at least one non-brittle and at least one brittle vehicle. The at least one brittle vehicle can preferably be the same vehicle (c) or a mixture of vehicle(s) as used for the preparation of the mixture containing crystalline lopinavir (a) and brittle vehicle (c). The at least one non-brittle vehicle can be preferably one as described above and further preferably having binding properties.

With regard to the excipient(s) (d) used in the step (iv), it is referred to the above-mentioned pharmaceutically acceptable excipient(s) (d).

In step (v), the mixture of step (iv) is processed into an oral dosage form. Step (v) can comprise, for example, compressing the mixture of step (iv) into tablets or filling the mixture of step (iv) into capsules, sachets or stick-packs. Preferably the mixture is compressed into tablets.

In an embodiment, the processing of the mixture of step (iv) into an oral dosage form can be done by filling the mixture of step (iv) into capsules, preferably hard shell capsules. For this filling of the mixture of step (iv) into capsules, dependent dosing systems (for example an auger) or preferably independent dosing systems (for example MG2, Matic (IMA)) can be used.

In a preferred embodiment, the mixture of step (iv) is compressed into tablets, for example on a rotary press, e.g. on a Fette® (Fette GmbH, Germany) or a Riva® Piccola (Riva, Argentina) or an eccentric press, e.g. a Korsch® EKO. The compression force usually ranges from 1 to 50 kN, preferably 3 to 40 kN. The resulting tablets preferably have a hardness of 30 to 400 N, more preferred 50 to 325 N, still more preferred from 65 to 275 N, in particular from 85 to 225 N, wherein the hardness is measured according to Ph. Eur., 6.0, Chapter 2.9.8.

Further, the tablets of the invention preferably have contents of active agent(s) which lie within the concentration of 90 to 110%, preferably 95 to 105%, especially preferred from 98 to 102% of the average content of the active agents(s). This "content uniformity" is determined with a test in accordance with Ph. Eur., 6.0, Chapter 2.9.6. According to that test, the content of the active agents of each individual tablet out of 20 tablets must lie between of 90 to 110%, preferably 95 to 105%, especially 98 to 102% of the average content of the active agents(s). Therefore, the content of the active drugs in each tablet of the invention differs from the average content of the active agent by at most 10%, preferably by at most 5% and especially by at most 2%.

In addition, the resulting tablets preferably have a friability of less than 5%, particularly preferably less than 2%, especially less than 1%. The friability is determined in accordance with Ph. Eur., 6.0, Chapter 2.9.7. The friability of tablets generally refers to tablets without coating.

The dosage form of the invention tablets may be a peroral tablet which can be swallowed unchewed. The tablet can preferably be film-coated.

Generally, film coatings which do not affect the release of the active agent(s) and film coatings affecting the release of the active agent(s) can be employed with tablets according to invention. The film coatings which do not affect the release of the active agent(s) are preferred.

Preferred examples of film coatings which do not affect the release of the active ingredient can be those including poly (meth)acrylate, methylcellulose (MC), hydroxypropyl methylcellulose (HPMC), hydroxypropyl cellulose (HPC), hydroxyethyl cellulose (HEC), polyvinyl pyrrolidone (PVP) and mixtures thereof. These polymers can have a weight-average molecular weight of 10,000 to 150,000 g/mol.

In an alternative preferred embodiment, the film coating can affect the release of the active agent. Examples for film coatings affecting the release of the active agent are gastric juice resistant film coatings and retard coatings.

Further, the coating can be free from active ingredient. However, it is also possible that the coating can contain an active ingredient (lopinavir and/or ritonavir, preferably only ritonavir). In such a case, this amount of active ingredient would function as an initial dose. In such a case, the coating preferably can comprise 1 to 45 wt %, preferably 5 to 35 wt %, most preferably 10 to 30 wt % of lopinavir or ritonavir, based on the total amount of lopinavir or ritonavir contained in the tablet.

In the preferred case that the film coating does not contain an active agent (a) or (b), said coating can have a thickness of 2 µm to 100 µm, preferably from 20 to 60 µm. In case of a coating containing an active agent (a) or (b), the thickness of the coating is usually 10 µm to 200 µm, preferably from 50 to 125 µm.

The oral dosage form of the present invention can preferably be employed in the treatment and prevention of infection caused by viruses, especially infection caused by HIV viruses.

When treating the diseases which are indicated for the active agent or the combination of active agents in the oral dosage forms of the invention, satisfactory results are usually obtained when lopinavir contained in the dosage form is administered in a daily dose of 100 to 1000 mg, preferably 160 to 960 mg, more preferably 200 to 900 mg and particularly 400 to 800 mg. For the same purpose, ritonavir contained in the dosage form is administered in a daily dose of 25 to 250 mg, preferably 40 to 240 mg, more preferably 50 to 225 mg and particularly 100 to 200 mg. In the same doses, applications less than once a day are possible, such as every two, three or four days, for example in a delayed-release formulation. The dosing regimen may be varied within or even outside this frame in order to achieve the optimum treatment results.

In a preferred embodiment the composition and/or the dosage form according to the invention provides an immediate release ("IR") of lopinavir/ritonavir. This means that the release profile of the dosage form of the invention according to USP method (paddle, 900 ml, water with 0.06 M C12E10 (polyoxyethylene-10-lauryl ether, 75 rpm, 37° C.) after 10 minutes usually indicates a content release of at least 20%, after 20 minutes a content release of at least 30%, after 30 minutes a content release of at least 45% and after 45 minutes a content release of at least 55%.

EXAMPLES

Co-Milling

Example 1

Crystalline lopinavir was milled for 3 hours with microcrystalline cellulose (Avicel® PH101), intragranular phase, and fumed silica (Aerosil® 200) in a planetary ball mill PM100 from Retsch®. After milling, a DSC showed that lopinavir remained in a crystalline form Microcrystalline cellulose (Avicel® PH101), extragranular phase, lactose monohydrate+povidone (Ludipress® LCE) and $Al_2O_3 \cdot MgO \cdot 1.7SiO_2 \cdot xH_2O$ (Neusilin®) were granulated with sorbitan laurate (Span® 20) in a Diosna® P1-6-high-sheer mixer. Afterwards the granules were sieved through a 500 μm sieve.

Ritonavir and copovidone (Kollidon® VA64) were blended in a Turbula® T10B Shaker-Mixer for 5 minutes.

All ingredients, except sodium stearyl fumarate, were blended in a Turbula® T10B Shaker-Mixer for 15 minutes. After addition of sodium stearyl fumarate and blending for further 5 minutes, the powdery blend was compressed on an eccentric press Korsch® EKO to 16.2 mm oblong tablets (600 mg) with a hardness of approximately 110 N (pressure force approximately 7.2 kN) each, containing

| Intragranular | |
| --- | --- |
| Lopinavir | 100 mg (16.67%) |
| Microcrystalline cellulose | 50 mg (8.33%) |
| Fumed silica | 12 mg (2.00%) |
| Extragranular | |
| Ritonavir | 25 mg (4.17%) |
| Lactose monohydrate + Povidon | 174 mg (29.00%) |
| Copovidone | 70 mg (11.67%) |
| Crospovidone | 60 mg (10.00%) |
| Microcrystalline cellulose | 22 mg (3.67%) |
| Sorbitan laurate | 40 mg (6.67%) |

-continued

| $Al_2O_3 \cdot MgO \cdot 1.7SiO_2 \cdot xH_2O$ | 40 mg (6.67%) |
| --- | --- |
| Sodium stearyl fumarate | 7 mg (1.17%) |

Parameters of Co-Milling Process

| milling time | 3 h |
| --- | --- |
| wheel speed | 150 $min^{-1}$ |
| break time interval | 5 min |
| break time | 5 min |
| direction reversal interval | every break time |

Comparative Example

The comparative example corresponds to Example 3 of patent application EP 1 663 183 B1.

Copovidone was blended with sorbitan monolaurate (Span 20) in a Diosna high-shear mixer. The resulting granules were mixed with ritonavir, lopinavir and colloidal silica. The powdery mixture was then fed into a twin-screw extruder with a melt temperature of 119° C. The extrudate was cut into pieces and allowed to solidify. The extruded pieces were milled using a co-mill from Retsch. The milled material was blended with sodium stearyl fumarate and colloidal silica for 10 minutes. The powdery blend was compressed on an eccentric press EKO from Korsch to tablets (601 mg), each containing

| Lopinavir | 100 mg |
| --- | --- |
| Ritonavir | 25 mg |
| Copovidone | 427 mg |
| Sorbitan monolaurate | 42 mg |
| Collodial silica | 6 mg |
| Sodium stearyl fumarate | 1 mg |

Figure 2:
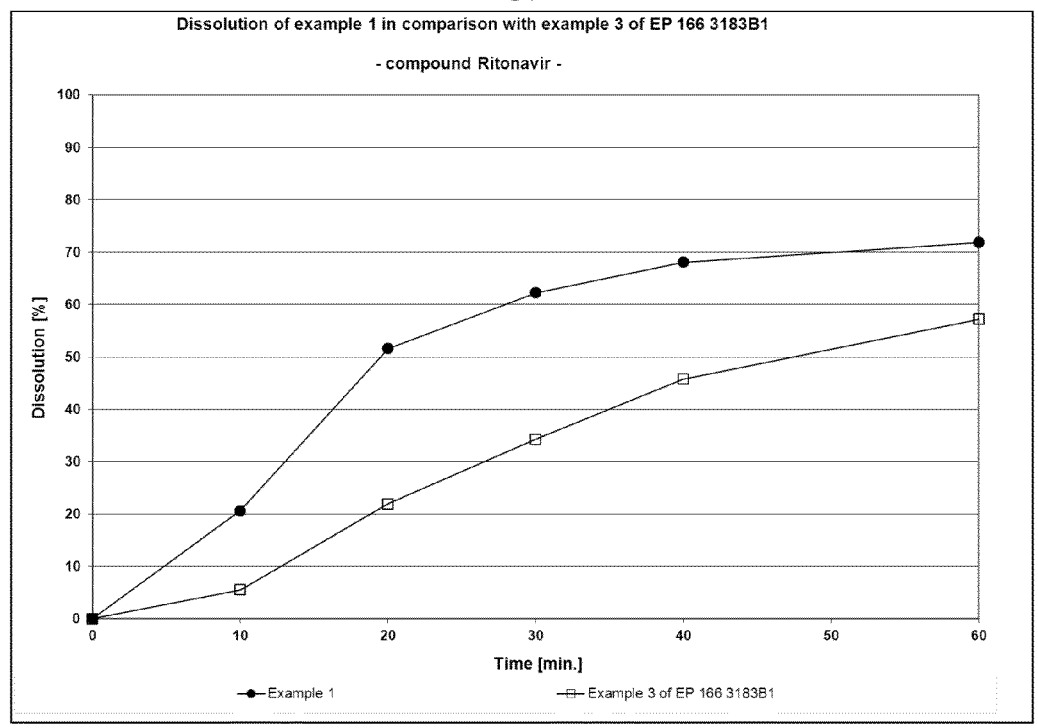

As can be seen from FIGS. 1 and 2, the tablet according to the present Example 1 shows superior dissolution profiles for both lopinavir and ritonavir compared to the tablet prepared according to example 3 of EP 1 663 183 B1. In particular, the dissolution profiles of both active agents of the present tablet do not show any lag time.

The invention claimed is:
1. An oral dosage form comprising
   10 to 35 wt % of crystalline lopinavir being present in a mixture with 10 to 50 wt % of a brittle vehicle,
   2 to 9 wt % of crystalline ritonavir,
   0 to 4 wt % of glidant,
   10 to 35 wt % of filler,
   3 to 17 wt % of disintegrant,
   2 to 15 wt % of surfactant, and
   0.3 to 2.5 wt % of lubricant, based on the total weight of the dosage form wherein
   the crystalline lopinavir comprises hydrated polymorphic Form I of lopinavir;
   the average particle diameter ($D_{50}$-value) of the crystalline lopinavir is from about 0.1 μm to about 50 μm;
   the crystalline ritonavir comprises polymorphic Form I of ritonavir, and lopinavir is 95 to 99.9% by weight of crystalline lopinavir and 0.1 to 5% by weight of non-crystalline lopinavir and ritonavir is 95 to 99.9% by weight of crystalline ritonavir and 0.1 to 5% by weight of non-crystalline ritonavir.
2. The oral dosage form according to claim 1, wherein the brittle vehicle has a yield pressure of from 80 MPa to 500 MPa.

3. The oral dosage form according to claim 1, wherein the brittle vehicle is an organic polymer or an inorganic substance.

4. The oral dosage form according to claim 1, wherein the brittle vehicle is microcrystalline cellulose.

5. The oral dosage form according to claim 1, wherein the crystalline lopinavir further comprises polymorphic Form III of lopinavir.

6. The oral dosage form according to claim 1, wherein the weight ratio of crystalline lopinavir to brittle vehicle is from 1:5 to 5:1.

7. The oral dosage form according to claim 1, wherein the mixture of crystalline lopinavir and brittle vehicle is obtained by a milling process, preferably by a co-milling process.

8. The oral dosage form according to claim 1, wherein the dosage form comprises an intragranular phase comprising the crystalline lopinavir and the brittle vehicle; and an extragranular phase comprising the crystalline ritonavir and optionally a non-brittle vehicle.

9. The oral dosage form according to claim 8, wherein the intragranular phase comprises the brittle vehicle, preferably having a $T_g$ of more than 50° C., and the extragranular phase comprises the non-brittle vehicle.

10. The oral dosage form according to claim 1, wherein the oral dosage form is in form of a capsule or a tablet.

11. A method for preparing an oral dosage according to claim 1 comprising
  (i) providing a mixture of the crystalline lopinavir and the brittle vehicle,
  (ii) processing the mixture of step (i) wherein it is assured that the lopinavir is maintained in crystalline form, thereby forming a pharmaceutical composition,
  (iii) optionally granulating the pharmaceutical composition from step (ii) to form granules,
  (iv) mixing the pharmaceutical composition of step (ii) or the granules of step (iii) with crystalline ritonavir thereby forming a crystalline ritonavir pharmaceutical composition, and
  (v) processing the crystalline ritonavir pharmaceutical composition of step (iv) into an oral dosage form.

12. The method according to claim 11, wherein processing of step (ii) comprises a co-milling process.

* * * * *